(12) United States Patent
Seitz et al.

(10) Patent No.: US 10,858,388 B2
(45) Date of Patent: *Dec. 8, 2020

(54) SELECTIVE PROGESTERONE RECEPTOR MODULATOR (SPRM) REGIMEN

(71) Applicant: BAYER PHARMA AKTIENGESELLSCHAFT, Berlin (DE)

(72) Inventors: Christian Seitz, Zeuthen (DE); Rudolf Knauthe, Glienicke (DE); Susan Zeun, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/214,515

(22) Filed: Dec. 10, 2018

(65) Prior Publication Data

US 2019/0211053 A1 Jul. 11, 2019

Related U.S. Application Data

(62) Division of application No. 15/575,088, filed as application No. PCT/EP2016/061037 on May 17, 2016, now abandoned.

(30) Foreign Application Priority Data

May 18, 2015 (EP) .................................. 15001475

(51) Int. Cl.
*A61P 15/08* (2006.01)
*C07J 31/00* (2006.01)
*A61K 31/567* (2006.01)
*A61P 15/00* (2006.01)

(52) U.S. Cl.
CPC .......... *C07J 31/006* (2013.01); *A61K 31/567* (2013.01); *A61P 15/00* (2018.01)

(58) Field of Classification Search
CPC ...................................................... A61P 15/08
See application file for complete search history.

(56) References Cited

U.S. PATENT DOCUMENTS

| 8,278,469 | B2 | 10/2012 | Schwede et al. |
| 9,085,603 | B2 | 7/2015 | Schwede et al. |
| 9,717,739 | B2 | 8/2017 | Schwede et al. |
| 10,155,004 | B2 | 12/2018 | Schwede et al. |
| 2011/0112057 | A1 | 5/2011 | Fuhrmann et al. |
| 2012/0014967 | A1 | 1/2012 | Masat et al. |
| 2012/0094969 | A1 | 4/2012 | Schwede et al. |
| 2012/0149670 | A1 | 6/2012 | Schwede et al. |
| 2015/0342962 | A1 | 12/2015 | Schwede et al. |
| 2017/0202857 | A1 | 7/2017 | Schwede et al. |
| 2018/0155388 | A1 | 6/2018 | Seitz et al. |
| 2018/0369257 | A1* | 12/2018 | Schultze-Mosgau ........ A61K 38/09 |

FOREIGN PATENT DOCUMENTS

| DE | 10 2009 034 362 | | 1/2011 | |
| EP | 0 057 115 | A2 | 8/1982 | |
| JP | 2013519641 | A | 5/2013 | |
| WO | 98/34947 | A1 | 8/1998 | |
| WO | 2004/098517 | A2 | 11/2004 | |
| WO | 2009/134178 | A1 | 11/2009 | |
| WO | 2011/009531 | A2 | 1/2011 | |
| WO | WO 2014/050106 | | 4/2014 | |
| WO | WO 2014/070517 | | 5/2014 | |
| WO | WO 2014/166971 | | 10/2014 | |
| WO | WO 2014/167510 | | 10/2014 | |
| WO | WO-2014166971 | A1 * | 10/2014 | ........... A61K 31/567 |

OTHER PUBLICATIONS

International Search Report for PCT/EP2016/061037, dated Oct. 25, 2016, 6 pages.
Wagenfeld, et al., "BAY 1002670: a novel, highly potent and selective progesterone receptor modulator for gynaecological therapies," Human Reprod., (2013), vol. 28, No. 8: 2253-64.
Spitz, et al., "Clinical utility of progesterone receptor modulators and their effect on the endometrium," Current Opinion in Obstetrics and Gynecology, (2009), vol. 21: 318-24.
Fuhrmann, et al., "Synthesis and Biological Activity of a Novel, Highly Potent Progesterone Receptor Antagonist," J. Med. Chem., (2000), vol. 43: 5010-16.
Donnez, et al., "Ulipristal Acetate versus Leuprolide Acetate for Uterine Fibroids," The New England Journal of Medicine, (2012), vol. 366, No. 5: 421-32.

* cited by examiner

*Primary Examiner* — John S Kenyon
(74) *Attorney, Agent, or Firm* — McBee Moore & Vanik IP, LLC

(57) ABSTRACT

The invention is directed to a pharmaceutical composition comprising a progesterone receptor antagonist namely (11β,17β)-17-Hydroxy-11-[4-(methylsulphonyl)phenyl]-17-(pentafluoroethyl)estra-4,9-dien-3-one for the treatment and/or prophylaxis of Uterine Fibroids (myomas, uterine leiomyoma) that is administered to a patient diagnosed with Uterine Fibroids following a specific regimen. Additionally, the invention is directed to a method for treating Uterine Fibroids (myomas, uterine leiomyoma) and/or for reducing Uterine Fibroids (myomas, uterine leiomyoma) size and symptoms related to Uterine Fibroids following a specific regimen as well as treatment of Heavy Menstrual Bleeding (HMB).

18 Claims, 7 Drawing Sheets

SELECTIVE PROGESTERONE RECEPTOR MODULATOR (SPRM) REGIMEN

CROSS REFERENCE

Figure 1:
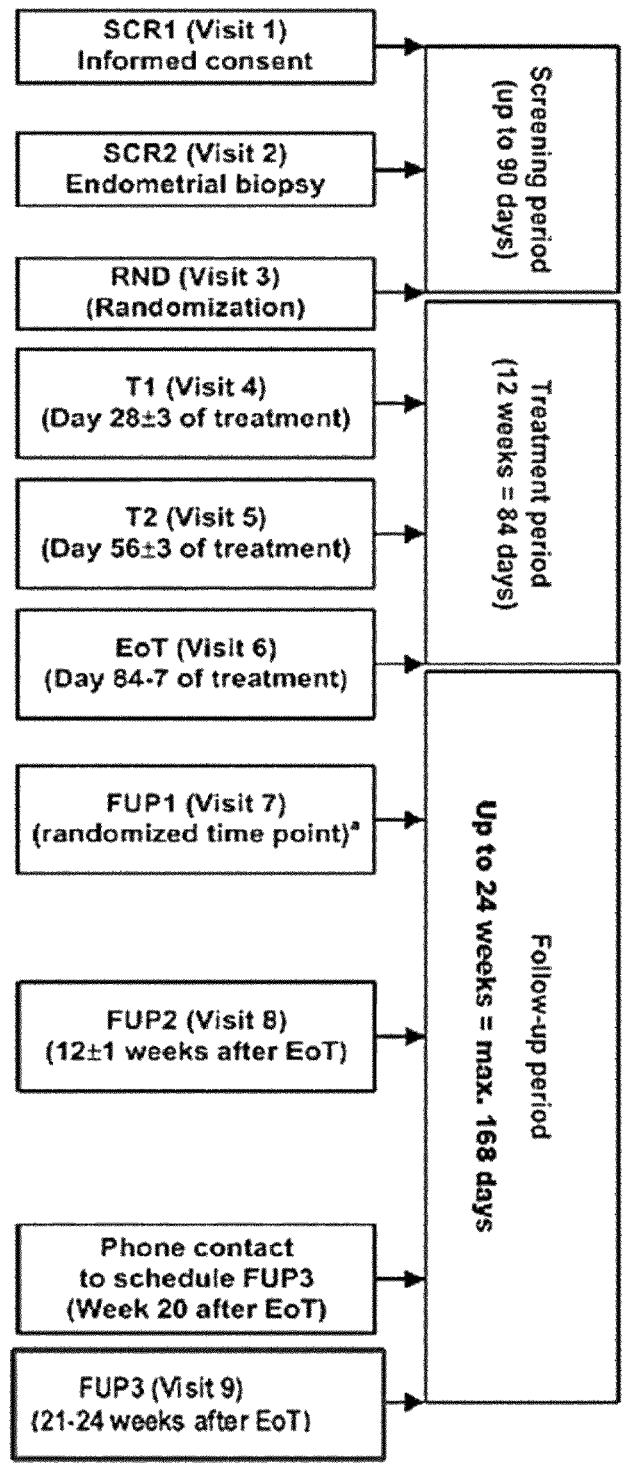

This application is a divisional of U.S. patent application Ser. No. 15/575,088, filed Nov. 17, 2017, pending, which is the U.S. National Phase of International Application No. PCT/EP2016/061037 filed May 17, 2016, which designated the U.S. and claims priority to European Patent Application No. 15001475.1 filed May 18, 2015, the entire contents of each of which are hereby incorporated by reference.

The invention is directed to a pharmaceutical composition comprising a progesterone receptor modulator namely (11β,17β)-17-Hydroxy-11-[4-(methylsulphonyl)phenyl]-17-(pentafluoroethyl)estra-4,9-dien-3-one for the treatment and/or prophylaxis of Uterine Fibroids (myomas, uterine leiomyoma) that is administered daily to a patient diagnosed with Uterine Fibroids following a specific regimen.

Additionally, the invention is directed to a method for treating Uterine Fibroids (myomas, uterine leiomyoma) and/or for reducing Uterine Fibroids (myomas, uterine leiomyoma) size and symptoms associated with Uterine Fibroids following a specific regimen as well as treatment of Heavy Menstrual Bleeding (HMB).

BACKGROUND

Uterine Fibroids (also called Uterine leiomyomas or myomas) are common benign tumors of the myometrium, which are reported to occur in approximately 30-40% of all women of reproductive age. They may remain asymptomatic, or cause bleeding abnormalities and/or bulk-related symptoms depending on their number, size and location. Various medications are used for symptom-oriented therapy in minor disease (e.g. combined oral contraceptives, progestogens, iron supplements). For short-term therapy and/or as a precursor to surgery, gonadotropin-releasing hormone agonists represent the most effective medical treatment. However, their use is restricted to 6 months due to hypo-estrogenic side effects. For definite treatment of symptomatic leiomyomas, therapeutic options are mainly surgical so far. Uterine Fibroids are the leading cause for hysterectomy. Hysterectomy is at present time the only definitive treatment and eliminates the possibility of recurrence.

Various studies suggested steroid-dependence of fibroids growth in which progesterone has a critical role. This is supported by the fact, that Progesterone Receptor (PR) antagonists—like mifepristone (RU 486)—have been shown to decrease the size of fibroids and related symptoms. Therefore, PR antagonists might offer a promising therapeutic alternative meeting the need for medical long-term treatment of symptomatic fibroids with an orally effective agent lacking clinically relevant side effects. Mifepristone (RU 486) was disclosed in EP057115.

Spitz et al. Current Opinion in Obstetrics and Gynecology, 2009, 21:318-324 discloses compounds being effective in the treatment of Uterine Fibroids where that are associated with a reduction in pain and bleeding and improvement in quality of life and decrease in fibroids size. Long-term treatments are associated with endometrial thickening confirmed by ultrasound and histological changes of the endometrium. The endometrial change such as endometrial thickening seems to be connected to cystic glandular dilatation.

Progesterone receptor antagonists with a fluorinated 17α-side chain were published in WO 98/34947 and Fuhrmann et al., J. Med. Chem. 43, 5010-5016 (2000).

In PEARL I and PEARL II trial (N Engl J Med. 2012; 366:409-420) women with excessive uterine bleeding due to the presence of fibroids were randomized to ulipristal acetate (5 mg vs. 10 mg orally once daily) vs. placebo or intramuscular injections of leuprolide acetate for up to 13 weeks.

WO2009/134178 discloses methods for treating endometrial proliferation wherein progesterone antagonists is used such as CDB-4124 in a six-month treatment regimen. Unfortunately, administration of a relatively low concentration of CDB-4124 results in a substantial thickening of the endometrium during treatment.

WO2004/098517 discloses a regimen in which a female is administered a combined dosage form of estrogen and progestin for more than 50 consecutive days.

SUMMARY

The invention is directed to a pharmaceutical composition comprising (11β,17β)-17-Hydroxy-11-[4-(methylsulphonyl)phenyl]-17-(pentafluoroethyl)estra-4,9-dien-3-one (Compound 1) of formula

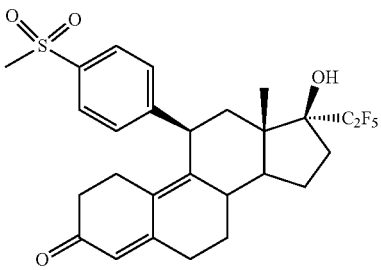

or salts, solvates or solvates of the salts, including all crystal modifications thereof for the treatment and/or prophylaxis of Uterine Fibroids (myomas, uterine leiomyoma) wherein Compound 1 is administered during a period of twelve (12) weeks up to twenty-four (24) weeks followed by a break period wherein administration of Compound 1 is discontinued until one (1) or two (2) bleeding episodes occur; optionally administration and break periods are repeated at least one (1) time.

Additionally, the invention is directed to a method for treating Uterine Fibroids and reducing Uterine Fibroids size and symptoms associated with Uterine Fibroids as well as for treating Heavy Menstrual Bleeding (HMB) by administrating to a patient a pharmaceutical composition comprising Compound 1.

Compound 1 is a potent Selective Progesterone Receptor Modulator (SPRM) and more particularly a competitive Progesterone Receptor (PR) antagonist creating alternatives for the treatment of Uterine Fibroids. Amenorrhea was observed in healthy subjects treated with compound 1 that was originally disclosed in WO2011/009531A1. Amenorrhea corresponds to the major objective of the treatment i.e. control of excessive uterine bleeding. It has been surprisingly found that long term treatment with Compound 1 is safe for patient in need. Indeed, amenorrhea was observed at early stage and with high intensity Further, ovulation inhibition was observed, pelvic pain was found to be reduced, no endometrial hypertrophy was reported (TEAE), and uterine fibroids size was clearly reduced. To conclude, no major safety findings were reported.

Additionally, it was found that short break periods (with one or two bleeding episodes) resolve PAECs already after one bleeding.

DESCRIPTION

In a first aspect, the invention is directed to a pharmaceutical composition comprising (11β,17β)-17-Hydroxy-11-[4-(methylsulphonyl)phenyl]-17-(pentafluoroethyl)estra-4,9-dien-3-one (Compound 1)
of formula

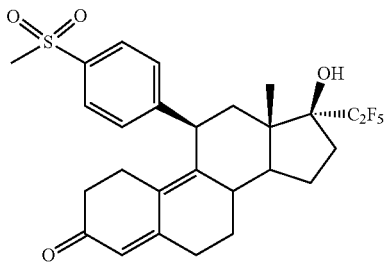

or salts, solvates or solvates of the salts, including all crystal modifications thereof for the treatment and/or prophylaxis of Uterine Fibroids (myomas, uterine leiomyoma) wherein Compound 1 is administered during a period of four (4) weeks to one (1) year, preferably, twelve (12) weeks up to twenty-four (24) weeks.

In one embodiment, the pharmaceutical composition is directed to the treatment and/or prophylaxis of Uterine Fibroids wherein Compound 1 is administered during a period of twelve (12) weeks up to twenty-four (24) weeks followed by a break period wherein administration of Compound 1 is discontinued until one (1) or two (2) bleeding episodes occur; optionally administration and break periods are repeated at least one (1) time.

In one embodiment, the pharmaceutical composition is directed to the treatment and/or prophylaxis of Uterine Fibroids wherein additionally amenorrhea is reached during treatment. Preferably, amenorrhea is reached at least after 3 weeks of administration. Preferably, amenorrhea is reached in at least 90% of patients treated with Compound 1 after 3 weeks or 12 weeks. More preferably, amenorrhea is reached in at least 90% of patients treated with Compound 1 after 3 weeks.

In one embodiment, the pharmaceutical composition is directed to the treatment and/or prophylaxis of Uterine Fibroids wherein additionally ovulation inhibition is reached during step a). Preferably, ovulation inhibition is reached at least after 3 weeks of administration.

In one embodiment, the pharmaceutical composition is directed to the treatment and/or prophylaxis of Uterine Fibroids wherein Compound 1 is administered daily.

In one embodiment, the pharmaceutical composition is directed to the treatment and/or prophylaxis of Uterine Fibroids wherein Compound 1 is administered daily at a dose of 1 mg to 5 mg.

In one embodiment, the pharmaceutical composition is directed to the treatment and/or prophylaxis of Uterine Fibroids wherein administration period of Compound 1 is repeated as necessary.

Preferably, administration period of Compound 1 is repeated at least one (1) time but no more than five (5) times.

More preferably, administration period of Compound 1 is repeated at least two (2) to three (3) times.

In one embodiment, the invention is directed to a pharmaceutical composition comprising (11β,17β)-17-Hydroxy-11-[4-(methylsulphonyl)phenyl]-17-(pentafluoroethyl)estra-4,9-dien-3-one (Compound 1)
of formula

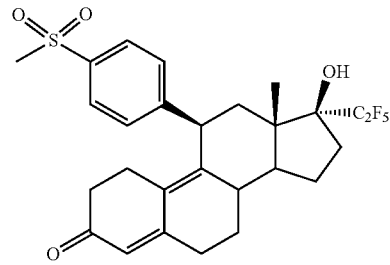

or salts, solvates or solvates of the salts, including all crystal modifications thereof for the treatment and/or prophylaxis of Uterine Fibroids (myomas, uterine leiomyoma) wherein Compound 1 is administered during a period of twelve (12) weeks, sixteen (16) weeks, twenty (20) weeks or twenty-four (24) weeks followed by a break wherein administration of Compound 1 is discontinued until one (1) or two (2) bleeding episodes occur; optionally administration and break periods are repeated at least one (1) time.

In one embodiment, the invention is directed to a pharmaceutical composition comprising (11β,17β)-17-Hydroxy-11-[4-(methylsulphonyl)phenyl]-17-(pentafluoroethyl)estra-4,9-dien-3-one (Compound 1)
of formula

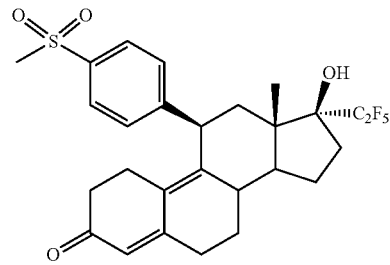

or salts, solvates or solvates of the salts, including all crystal modifications thereof for the treatment and/or prophylaxis of Uterine Fibroids (myomas, uterine leiomyoma) wherein 2 mg of Compound 1 is administered daily during a period of twelve (12) weeks, sixteen (16) weeks, twenty (20) weeks or twenty-four (24) weeks followed by a break wherein administration of Compound 1 is discontinued until one (1) or two (2) bleeding episodes occur; optionally administration and break periods are repeated at least one (1) time.

In a second aspect, the invention is directed to a method for treating Uterine Fibroids (myomas, uterine leiomyoma) by administrating to a patient a pharmaceutical composition comprising (11β,17β)-17-Hydroxy-11-[4-(methylsulphonyl)phenyl]-17-(pentafluoroethyl)estra-4,9-dien-3-one (Compound 1)
of formula

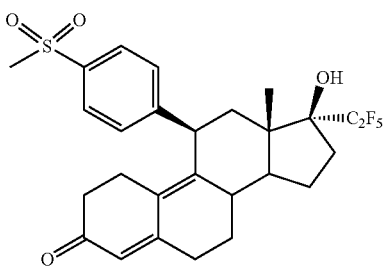

or salts, solvates or solvates of the salts, including all crystal modifications thereof wherein Compound 1 is administered during a period of four (4) weeks to one (1) year, preferably, twelve (12) weeks up to twenty-four (24) weeks followed by a break wherein administration of Compound 1 is discontinued until one (1) or two (2) bleeding episodes occur; optionally administration and break are repeated at least one (1) time.

In one embodiment, the present invention is directed to a method for treating Uterine Fibroids wherein compound 1 is to be administered during period of four (4) weeks to one (1) year.

In one embodiment, the present invention is directed to a method for treating Uterine Fibroids wherein compound 1 is to be administered during period of twelve (12) weeks up to twenty-four (24) weeks.

In one embodiment, the pharmaceutical composition is directed to the treatment and/or prophylaxis of Uterine Fibroids wherein additionally amenorrhea is reached during treatment Preferably, amenorrhea is reached at least after 3 weeks of administration. Preferably, amenorrhea is reached in at least 90% of patients treated with Compound 1 after 3 weeks or 12 weeks. More preferably, amenorrhea is reached in at least 90% of patients treated with Compound 1 after 3 weeks.

In one embodiment, the present invention is directed to a method for treating Uterine Fibroids wherein additionally ovulation inhibition is reached during treatment. Preferably, ovulation inhibition is reached at least after 3 weeks of administration.

In one embodiment, the present invention is directed to a method for treating Uterine Fibroids wherein Compound 1 is administered daily.

Embodiments and preferred features as described above are herein included.

In a third aspect, the invention is directed to a method for reducing Uterine Fibroids (myomas, uterine leiomyoma) size and/or reducing symptoms associated with Uterine Fibroids by administrating to a patient a pharmaceutical composition comprising (11β,17β)-17-Hydroxy-11-[4-(methylsulphonyl)phenyl]-17-(pentafluoroethyl)estra-4,9-dien-3-one (Compound 1) of formula

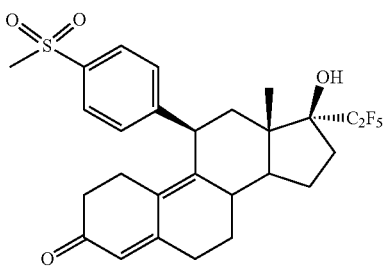

or salts, solvates or solvates of the salts, including all crystal modifications thereof wherein Compound 1 is administered during a period of four (4) weeks to one (1) year, preferably, twelve (12) weeks up to twenty-four (24) weeks followed by a break period wherein administration of Compound 1 is discontinued until one (1) or two (2) bleeding episodes occur; optionally administration and break are repeated at least one (1) time.

Reducing of Uterine Fibroids (myomas, uterine leiomyoma) size and/or reducing symptoms related to Uterine Fibroids is partial or in totality.

Symptoms associated with Uterine Fibroids are Heavy Menstrual Bleeding (HMB), pain or pressure like pelvic, backache or leg pains or pressures, prolonged menstrual periods, frequent urination or constipation.

In one embodiment, the present invention is directed to method for reducing Uterine Fibroids (myomas, uterine leiomyoma) size and/or reducing symptoms associated with Uterine Fibroids wherein compound 1 is to be administered during period of four (4) weeks to one (1) year.

In one embodiment, the present invention is directed to method for reducing Uterine Fibroids (myomas, uterine leiomyoma) size and/or reducing symptoms associated with Uterine Fibroids wherein compound 1 is to be administered during period of twelve (12) weeks up to twenty-four (24) weeks.

In one embodiment, the present invention is directed to method for reducing Uterine Fibroids (myomas, uterine leiomyoma) size and/or reducing symptoms associated with Uterine Fibroids wherein additionally amenorrhea is reached during treatment Preferably, amenorrhea is reached at least after 3 weeks of administration. Preferably, amenorrhea is reached in at least 90% of patients treated with Compound 1 after 3 weeks or 12 weeks. More preferably, amenorrhea is reached in at least 90% of patients treated with Compound 1 after 3 weeks.

In one embodiment, the present invention is directed to method for reducing Uterine Fibroids (myomas, uterine leiomyoma) size and/or reducing symptoms associated with Uterine Fibroids wherein additionally ovulation inhibition is reached during treatment. Preferably, ovulation inhibition is reached at least after 3 weeks of administration.

In one embodiment, the present invention is directed to a method for treating Uterine Fibroids wherein Compound 1 is administered daily.

Embodiments and preferred features as described above are herein included.

In a fourth aspect, the invention is directed to a method for treating Heavy Menstrual Bleeding (HMB) by administrating to a patient a pharmaceutical composition comprising (11β,17β)-17-Hydroxy-11-[4-(methylsulphonyl)phenyl]-17-(pentafluoroethyl)estra-4,9-dien-3-one (Compound 1) of formula

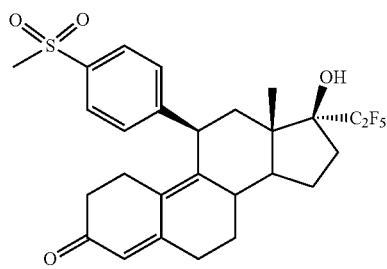

or salts, solvates or solvates of the salts, including all crystal modifications thereof wherein Compound 1 is administered during a period of four (4) weeks to one (1) year, preferably, twelve (12) weeks up to twenty-four (24) weeks followed by a break period wherein administration of Compound 1 is discontinued until one (1) or two (2) bleeding episodes occur; optionally administration and break are repeated at least one (1) time.

In one embodiment the invention is directed to a method for treating Heavy Menstrual Bleeding (HMB) wherein amenorrhea is reached during treatment. Preferably, amenorrhea is reached at least after 3 weeks of administration of Compound 1.

In one embodiment, the present invention is directed to method for treating Heavy Menstrual Bleeding (HMB) wherein compound 1 is to be administered during period of four (4) weeks to one (1) year.

In one embodiment, the present invention is directed to method for treating Heavy Menstrual Bleeding (HMB) wherein compound 1 is to be administered during period of twelve (12) weeks up to twenty-four (24) weeks.

In one embodiment, the present invention is directed to method for treating Heavy Menstrual Bleeding (HMB) wherein additionally amenorrhea is reached during treatment Preferably, amenorrhea is reached at least after 3 weeks of administration. Preferably, amenorrhea is reached in at least 90% of patients treated with Compound 1 after 3 weeks or 12 weeks. More preferably, amenorrhea is reached in at least 90% of patients treated with Compound 1 after 3 weeks.

In one embodiment, the present invention is directed to method for treating Heavy Menstrual Bleeding (HMB) wherein additionally ovulation inhibition is reached during treatment. Preferably, ovulation inhibition is reached at least after 3 weeks of administration.

In one embodiment, the present invention is directed to method for treating Heavy Menstrual Bleeding (HMB) wherein Compound 1 is administered daily.

In a fifth aspect, the invention is directed to a Compound 1 defined as (11β,17β)-17-Hydroxy-11-[4-(methylsulphonyl)phenyl]-17-(pentafluoroethyl)estra-4,9-dien-3-one of formula

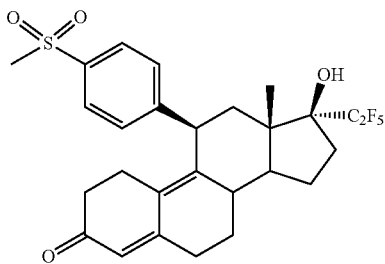

or salts, solvates or solvates of the salts, including all crystal modifications thereof for the use in a method for treating and/or prophylaxis of Uterine Fibroids wherein
 a) Compound 1 is administered daily during a period of four (4) weeks to one (1) year preferably ten (10) weeks up to twenty six (26) weeks.

In one embodiment, the present invention is directed to the use in a method for treating and/or prophylaxis of Uterine Fibroids wherein step a) is followed by
 b) a break period wherein administration of Compound 1 is discontinued and encompass one (1) or two (2) bleeding episodes and c) step a) and/or b) are/is repeated at least one (1) time.

In one embodiment, the present invention is directed to the use in a method for treating and/or prophylaxis of Uterine Fibroids wherein Compound 1 is administered daily during a period of twelve (12) weeks up to twenty-four (24) weeks.

Preferably step a) and/or b) are/is repeated at least one (1) time but no more than five (5) times. More preferably, step a) and/or b) are/is repeated at least two (2) to three (3) times.

In one embodiment, the present invention is directed to the use in a method for treating and/or prophylaxis of Uterine Fibroids wherein additionally amenorrhea is reached during treatment Preferably, amenorrhea is reached at least after 3 weeks of administration. Preferably, amenorrhea is reached in at least 90% of patients treated with Compound 1 after 3 weeks or 12 weeks. More preferably, amenorrhea is reached in at least 90% of patients treated with Compound 1 after 3 weeks.

In one embodiment, the present invention is directed to the use in a method for treating and/or prophylaxis of Uterine Fibroids wherein additionally ovulation inhibition is reached during treatment. Preferably, ovulation inhibition is reached at least after 3 weeks of administration.

In one embodiment, the present invention is directed to the use in a method for treating and/or prophylaxis of Uterine Fibroids wherein Compound 1 is administered daily in step a) at a dose of 1 mg to 5 mg.

Embodiments and preferred features as described above/below are herein included.

Preferred Features Applicable for First to Fifth Aspects:

Treatment of Uterine Fibroids according to the invention means that following administration of the pharmaceutical composition comprising Compound 1 the size of Uterine Fibroids is reduced partially or totally or known symptoms like Heavy Menstrual Bleeding (HMB) or pelvic pain related to Uterine Fibroids are reduced partially or are not anymore reported/detectable.

The patient is a human female in need of treatment due the presence of diagnosed Uterine Fibroids or suffering from Uterine Fibroids related symptoms, such as Heavy Menstrual Bleeding (HMB), pain or pressure like pelvic, backache or leg pains or pressures, prolonged menstrual periods, frequent urination or constipation.

Most common symptoms related to Uterine Fibroids are pelvic pain and heavy menstrual bleeding. Preferably, treated symptom is Heavy Menstrual Bleeding (HMB).

The pharmaceutical composition of present invention comprises Compound 1 that is preferably daily administrated to patient in a range of about 0.7 to 5 mg, 0.7 to 4.5 mg, 1 to 4.5 mg, 1 to 4 mg, 1.5 to 3.5 mg or 1.5 to 3 mg Compound 1 or salt thereof independently from each other. More preferably, Compound 1 is administrated to patient in range of about 0.7 to 5 mg, 1 to 4 mg or 1.5 to 3 mg. Even more preferably, Compound 1 is administrated to patient in range of about 1 to 5 mg or 1 to 4 mg. Even more preferably, 2 mg of Compound 1 is administrated.

Preferably, 0.5 mg, 0.7 mg, 1 mg, 2 mg, 3 mg, 4 mg, or 5 mg of Compound 1 is administrated to patient. More preferably, 2 mg, 3 mg or 4 mg of Compound 1 is administrated to patient. Even more preferably, 2 mg of Compound 1 is administrated.

It shall be understood that the dosage "about 2 mg" means any dosage from 1.5 to 2.5 mg of compound 1. Preferably, the dosage is of 2 mg of compound 1.

Compound 1 is administered during a period of four (4) weeks to one (1) year preferably eleven (11) weeks up to twenty five (25) weeks.

Preferably, Compound 1 is administered during a period of eleven (11) weeks up to thirteen (13) weeks, fifth teen (15) weeks up to seventeen (17) weeks, nineteen (19) weeks up to twenty-one (21) weeks or twenty-three (23) weeks up to twenty-five (25) weeks.

Compound 1 is administered during a period of twelve (12) weeks up to twenty-four (24) weeks.

Preferably, Compound 1 is administered during a period of twelve (12) weeks, sixteen (16) weeks, twenty (20) weeks or twenty-four (24) weeks.

More preferably, Compound 1 is administered during a period of twelve (12) weeks, or twenty-four (24) weeks.

Even more preferably, Compound 1 is administered during a period of twelve (12) weeks.

Even more preferably, Compound 1 is administered during a period of twenty-four (24) weeks.

More preferably, Compound 1 is administered during a period of sixteen (16) weeks, or twenty (20) weeks.

Even more preferably, Compound 1 is administered during a period of sixteen (16) weeks.

Even more preferably, Compound 1 is administered during a period of twenty (20) weeks.

Preferably, Compound 1 is administered during a period of twelve (12) weeks up to sixteen (16) weeks, sixteen (16) weeks up to twenty (20) weeks, or twenty (20) weeks up to twenty-four (24) weeks Preferably, Compound 1 is administrated daily.

Optionally, an administration-break of one (1) to four (4) days occurs during the period of twelve (12) weeks up to twenty-four (24) weeks of administration or any other period of administrations as defined above.

Administration period defined above shall be understood to comprise a variability of + or −1 or 2 days.

Preferably, one (1) bleeding episode occurs during the break period.

Preferably, two (2) bleeding episodes occur during the break period.

Optionally, administration and break period after administration are repeated at least one (1) time but no more than two (2) to ten (10) times. Repeated administration starts within the first 3 days of the first bleeding episode following the previous administration.

The first administration starts within the first ten (10) days of the female's menstrual cycle.

The patient undergoes no further menstruations during the course of treatment.

Additionally, the pharmaceutical composition comprises additionally a pharmaceutically acceptable excipient. Pharmaceutically acceptable excipient is defined as a filler (such as sugars, such as lactose, sucrose, dextrose and dextrates; sugar alcohols, such as mannitol, sorbitol and xylitol); carbonates and phosphates of alkaline earth metals, such as calcium carbonate and calcium phosphate; celluloses, such as powdered cellulose and microcrystalline cellulose; colloidal silica; titanium dioxide; kaolin; talc), or lubricants (such as magnesium stearate).

The invention encompasses all salts, solvates or solvates of the salts, including all crystal modifications of (11β,17β)-17-Hydroxy-11-[4-(methylsulphonyl)phenyl]-17-(pentafluoroethyl)estra-4,9-dien-3-one.

The pharmaceutical composition is in an appropriate form for intravenous (i.v.), intramuscular (i.m.) or oral administration. Preferably, oral form for administration is a dosage form such as tablet capsule or solution. Nevertheless, it may optionally be necessary to deviate from the stated amounts, namely depending on body weight, route of administration, individual response to the active substance, type of preparation and point of time or interval when application takes place. Thus, in some cases it may be sufficient to use less than the aforementioned minimum amount, whereas in other cases the stated upper limit must be exceeded. In the case of the administration of larger amounts it may be advisable to distribute these in several individual doses throughout the day.

Preferably, administration period of Compound 1 is repeated at least one (1) time but no more than five (5) times. More preferably, administration period of Compound 1 is repeated at least two (2) to three (3) times.

Definitions

The pharmaceutical composition can be in the form of an oral dosage form comprising additionally a pharmaceutically acceptable excipient and/or at least one or more other active substances, in particular active substances known for the treatment and/or prophylaxis of the aforementioned diseases.

Physiologically harmless salts of the compounds according to the invention are preferred as salts within the scope of the present invention. However, salts that are not suitable in themselves for pharmaceutical uses, but can for example be used for the isolation or purification of the compounds according to the invention, are also covered.

Physiologically harmless salts of the compound according to the invention comprise—when they contain a basic function—salts with inorganic or organic acids, in particular of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalene-disulphonic acid, acetic acid, trifluoroacetic acid, propionic acid, lactic acid, tartaric acid, malic acid, citric acid, fumaric acid, maleic acid and benzoic acid.

Physiologically harmless salts of the compound according to the invention comprise—when they contain an acid function—alkali metal salts, alkaline earth metal salts or ammonium salts, such as can be obtained by reaction with corresponding inorganic or organic bases. We may mention, for example and preferably, alkali metal salts (e.g. sodium and potassium salts), alkaline earth metal salts (e.g. calcium and magnesium salts) and ammonium salts, derived from ammonia or organic amines with 1 to 16 carbon atoms, such as, for example and preferably, ethylamine, diethylamine, triethylamine, ethyldiisopropylamine, monoethanolamine, diethanolamine, triethanolamine, bicyclo-hexylamine, dimethylamino-ethanol, procaine, dibenzylamine, N-methyl-morpholine, arginine, lysine, ethylenediamine, N-methyl piperidine, N-methyl glucamine, D-methyl glucamine, ethyl glucamine, 1,6-hexadiamine, glucosamine, N-methylglycine, 2-amino-1,3-propandiol, tris-hydroxymethyl-aminomethane and 1-amino-2,3,4-butanetriol.

Those forms of the compound according to the invention that display, in the solid or liquid state, adduct formation with solvent molecules, are designated as solvates within the scope of the invention. The solvent can be present in stoichiometric or even non-stoichiometric proportions. In the case of stoichiometric solvates, they are also called hemi-, (semi-), mono-, sesqui-, di-, tri-, tetra-, penta-, etc. solvates. Hydrates are a special form of solvates, in which the coordination takes place with water.

A bleeding episode is at least one day of menstrual bleeding.

Uterine Fibroids is reduced totally means that Uterine Fibroids cannot be detected by usual methods (Ultra sound).

The compound of invention is administered to patient in need of treatment and suffering from Uterine Fibroids and symptoms associated with Uterine Fibroids such as Heavy Menstrual Bleeding (HMB), pain or pressure like pelvic, backache or leg pains or pressures, prolonged menstrual periods, frequent urination or constipation. The patient in need are female mammal patient and more particularly human female.

The break period means a period of time where the administration to subject (human female) of Compound 1 is discontinued and where one (1) or two (2) bleeding episodes occur.

long term treatment corresponds to treatment of more than 3 months.

Sort term treatment corresponds to treatment of less than 3 months.

One year means 12 months.

The pharmaceutical efficacy of the compound according to the invention can be explained by their action as progesterone receptor antagonists, and thus by their antagonizing action on the progesterone receptor.

EXPERIMENTAL PART

The Compound 1 according to the invention displays an unforeseeable, valuable pharmacological, pharmacokinetic and pharmacodynamic profile of action.

The following examples serve to explain the invention without limiting it in any way.

Example 1: Synthesis Path of Compound 1

(11β,17β)-17-Hydroxy-11-[4-(methylsulphonyl) phenyl]-17-(pentafluoroethyl)estra-4,9-dien-3-one

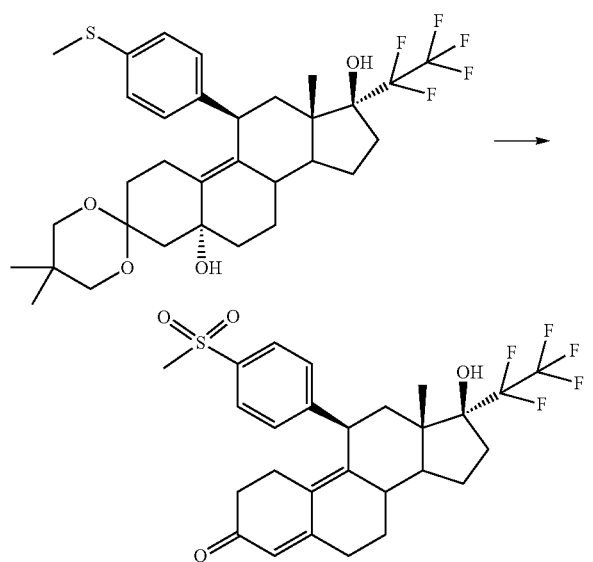

5 g of the compound described above was dissolved in a mixture of 140 ml THF and 140 ml methanol. A solution of 20 g Oxone® in 94 ml water was slowly added dropwise at 0° C. Then it was stirred for a further 3.5 hours at 0° C. Then a mixture of water and dichloromethane was added to the reaction mixture. The phases were separated and the aqueous phase was extracted several times with dichloromethane. The combined organic phases were washed with saturated aqueous sodium chloride solution, dried over sodium sulphate and concentrated under vacuum. The raw product was purified by silica gel chromatography. This gave 3.8 g of the title compound.

$^1$H-NMR (300 MHz, CDCl$_3$): δ=7.86 d (2H); 7.40 d (2H); 5.81 sbr (1H); 4.50 dbr (1H); 3.07 s (3H); 0.51 s (3H).

Example 2: Efficacy and Safety of Compound 1 in Patients Diagnosed with Uterine Fibroids Study Protocol:

Women, 18 to 50 years old, with Uterine Fibroids documented by transvaginal or abdominal ultrasound at screening with at least 1 Uterine Fibroids with largest diameter ≥3.0 cm and heavy menstrual bleeding (HMB) >80 mL are enrolled as subject in the study. The primary efficacy variable is amenorrhea (yes/no), defined as no scheduled bleeding/spotting after the end of the initial bleeding episode monitored until the end of the respective treatments.

Treatment groups A1, B1: 30 subjects each

Treatment groups A2, B2: 6 subjects each

A1: Compound 1: 2 mg (12 weeks), Compound 1: 2 mg (12 weeks),

A2: Placebo (12 weeks), Compound 1: 2 mg (12 weeks),

B1: Compound 1: 2 mg (12 weeks), 1 bleeding episode, Compound 1: 2 mg (12 weeks), B2: Placebo (12 weeks), 1 bleeding episode, Compound 1 2 mg (12 weeks).

Objective study: Presence of amenorrhea after 12 weeks and up to 24 weeks of treatment.

Amenorrhea is selected as the primary efficacy endpoint for assessing the Uterine fibroids pathology.

Example 3: Endometrium Thickness and PAEC 3-Month Treatment with Compound 1

A randomized, parallel-group, double-blind, placebo-controlled, multi-center study to assess efficacy of different doses of Compound 1 where primary efficacy variable is Endometrium thickness and secondary efficacy variable is PAEC in subjects with uterine fibroids over a 3-month treatment [1×12 weeks/84 days]

Study Protocol (No 15788):

Test drug: Compound 1

Doses: 0.5 mg, 1 mg, 2 mg, or 4 mg once daily

Route of administration: Oral

Duration of treatment: 1×12 weeks (84 days)

Reference drug: Placebo

Duration of treatment: 1×12 weeks (84 days)

Diagnosis and main criteria for inclusion:

Women, 18 to 50 years old, with uterine fibroids documented by transvaginal or abdominal ultrasound at screening with at least 1 uterine fibroid with largest diameter 3 cm and heavy menstrual bleeding (HMB) 80 ml were eligible for enrolment in the study.

Number of Women: 279 subjects (see "n" in table below)

Screening Period:

Following screening visit 1 (Visit 1), there was a screening period of up to 90 days to arrange for complete results of all baseline assessments. During the screening period, subjects have demonstrated eligibility including presence of at least 1 uterine fibroid of maximum 3 cm diameter and a diagnosis of HMB, defined as menstrual blood loss 80 ml assessed by menstrual pictogram (MP) during the bleeding episode following the screening visit 1 (Visit 1). Every effort was made to keep the duration of the screening period to a minimum. An endometrial biopsy was performed at the screening visit 2.

First Biopsy:

Biopsy during the screening period:

The first endometrial biopsy was performed on Day 9+/−2 of the first or second menstrual cycle after screening visit 1, i.e. at screening visit 2.

Second Biopsy:

Biopsy was determined by randomization. This means that subjects were randomized to the time point of the second biopsy and were informed about the group they are in, directly after randomization followed by stratification by dose group. Each subject had a biopsy at one of the following 4 time points: between Week 8 and Week 12 of treatment.

If a subject was randomized to this time point, the biopsy was scheduled on Day 9+/−2 of the first menstrual cycle after the treatment visit 2 (corresponding to Visit 5), i.e. during the last 4 weeks of study drug treatment. If no menstrual bleeding occurs between the treatment visit 2 (Visit 5) and the end of treatment (EoT) visit (Visit 6), the biopsy was performed at the end of treatment (EoT) visit (Visit 6).

Following the first menstrual bleeding after the end of treatment:

If a subject was randomized to this time point, the biopsy was scheduled on Day 9+/−2 of the first menstrual cycle after the end of treatment. If no menstrual bleeding occurs until 12 weeks after end of treatment, i.e. until the follow-up visit 2 (Visit 8), a biopsy was performed at the follow-up visit 2 (Visit 8) and induction of bleeding was considered.

Following the second menstrual bleeding after the end of treatment:

If a subject was randomized to this time point, the biopsy was scheduled on Day 9+/−2 of the second menstrual cycle after the end of treatment. If no menstrual bleeding occurs until 12 weeks after end of treatment, i.e. until the follow-up visit 2 (Visit 8), a biopsy was performed at the follow-up visit 2 (Visit 8) and induction of bleeding was considered.

Following the third menstrual bleeding after the end of treatment:

If a subject is randomized to this time point, the biopsy was scheduled on Day 9+1-2 of the third menstrual cycle after end of treatment. If no menstrual bleeding occurred until 12 weeks after end of treatment, i.e. until the follow-up visit 2 (Visit 8), a biopsy was performed at the follow-up visit 2 (Visit 8) and induction of bleeding was considered.

Third Biopsy:

At the end of follow-up, i.e. 21 to 24 weeks after end of treatment.

The third endometrial biopsy was performed at the follow-up visit 3 (Visit 9), which was scheduled on Day 9+/−2 of the menstrual cycle which started following Week 20 after the end of treatment. If no bleeding episode occurred, Visit 9 was performed 24 weeks after end of treatment, i.e. Visit 9 took place 21 to 24 weeks after the end of treatment in all subjects. If the second endometrial biopsy was performed less than 6 weeks before the scheduled date of the third endometrial biopsy and pathological findings were absent, the third endometrial biopsy was not required.

In certain situations, unscheduled endometrial biopsies should be performed in addition.

Treatment Period:

Eligible subjects were equally randomized to one of the treatment groups (Placebo, 0.5 mg, 1 mg, 2 mg, or 4 mg Compound 1). Treatment started during the first week of the menstrual cycle following randomization. The treatment period consisted of 12 weeks (84 days) of daily tablet intake.

Follow-Up Period:

After the end of treatment, subjects were followed up for 21 to 24 weeks (Follow-up period). If spontaneous menstrual bleeding did not occur until 12 weeks after the end of treatment, an additional transvaginal ultrasound (TVU) and endometrial biopsy was performed followed by induction of bleeding, if indicated. In case of findings that require further follow-up, additional visits were scheduled according to normal standard practice.

FIG. 1: Study Design overview

EoT: End of Treatment visit

FUP1, 2, 3: Follow-up visit 1, 2, 3

RND: Randomization visit

SCR1, 2: Screening visit 1, 2

T1, 2: Treatment visit 1, 2

Efficacy Measurement:

endometrial biopsies cervical smear transvaginal ultrasound TVU (endometrial thickness, ovaries)

Subjects that were detected with endometrial thickness (double layer)>18 mm (or suspicious bleeding pattern, e.g. continuous spotting, unusually heavy bleeding), were immediately evaluated by an additional endometrial biopsy.

Results:

Under treatment, no clear trend for an increase in endometrial thickness was observed. Endometrial thickness was measured after 3 months treatment, see table 1. At the end of follow-up, endometrial biopsies demonstrated benign endometrial histology changes (PAEC) and were reported in all available samples. It was no cases of hyperplasia.

Consequently, No treatment-emergent critical endometrial findings occurred.

Figure 2:
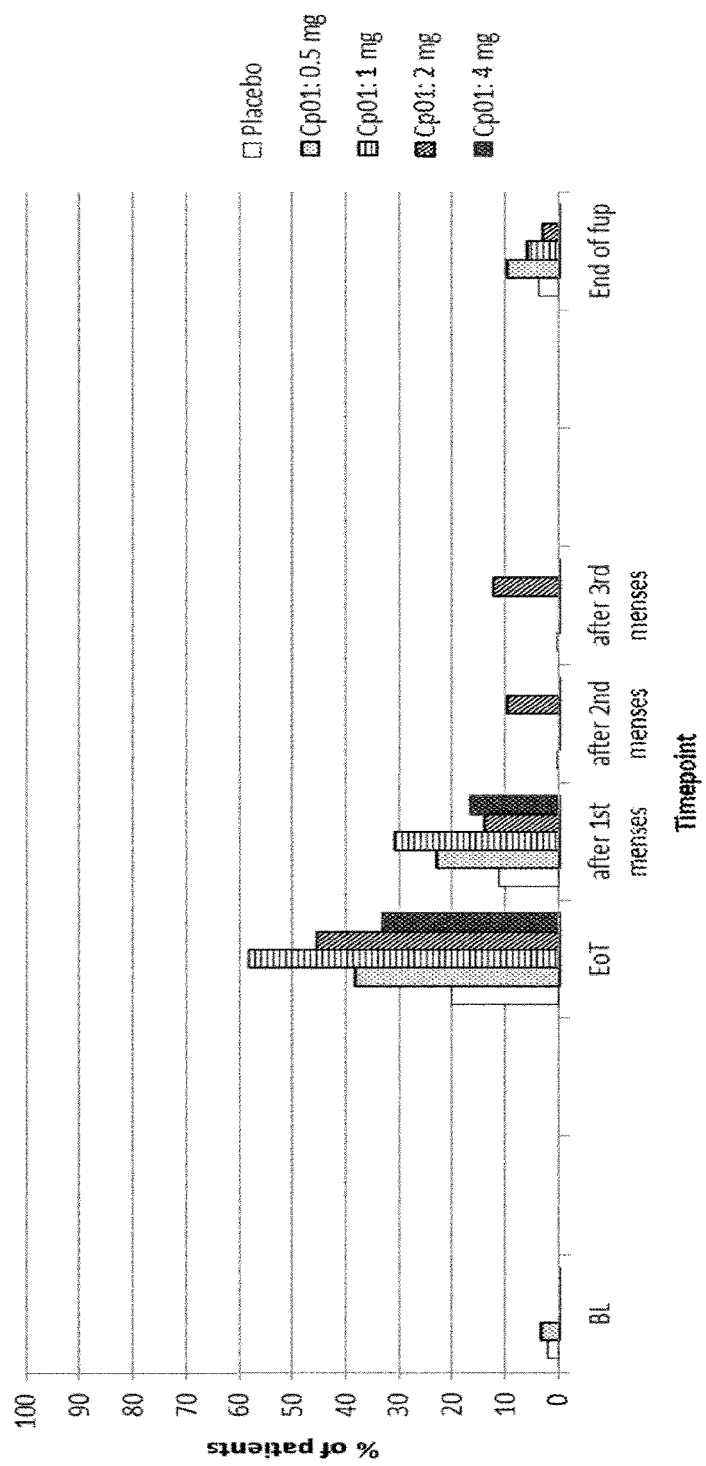

Additionally, PAECs (progesterone receptor modulator associated endometrial changes) returned to background level during follow-up, FIG. 2. Data indicate that PAECs are already resolved after one bleeding.

TABLE 1

| | Endometrial thickness after 3 months treatment | | | | |
|---|---|---|---|---|---|
| | Placebo n = 52 | 0.5 mg Cp01 n = 57 | 1 mg Cp01 n = 56 | 2 mg Cp01 n = 58 | 4 mg Cp01 n = 56 |
| Median endometrial thickness at EoT, mm (max, SD) | 8.5 (18.0, 3.9) | 9.0 (27.0, 5.2) | 10.0 (41.0, 7.0) | 7.5 (27.0, 4.7) | 8.5 (20.0, 4.9) |
| Subjects with maximum | 2 (3.6) | 2 (3.4) | 7 (12.5) | 2 (3.5) | 0 |

TABLE 1-continued

| Endometrial thickness after 3 months treatment | | | | | |
|---|---|---|---|---|---|
| | Placebo n = 52 | 0.5 mg Cp01 n = 57 | 1 mg Cp01 n = 56 | 2 mg Cp01 n = 58 | 4 mg Cp01 n = 56 |
| endometrium thickness >18 mm, n (%) | | | | | |

EoT: End of Treatment
Cp01: Compound 01
n: Number of Subjects
max: Maximum
SD: Standard Deviation
Safety set (n = 300)

FIG. 2: PAEC in biopsy after 1st/2nd/3rd bleeding episodes (menses). Pharmacodynamic effecs on the endometrium. Percentage of subjects with PAEC.
EoT: End of Treatment
BL: Baseline

Example 4 Amenorrhea 3-Month Treatment with Compound 1 and Ulipristal Acetate (UPA)

A randomized, parallel-group, double-blind, placebo-controlled, multi-center study to assess efficacy of different doses of Compound 1 where primary efficacy variable is Amenorrhea, in subjects with uterine fibroids over a 3-month treatment [1×12 weeks/84 days]
Study Protocol (No 15788):
Test drug: Compound 1
Doses: 0.5 mg, 1 mg, 2 mg, or 4 mg once daily
Route of administration: Oral
Duration of treatment: 1×12 weeks (84 days)
Reference drug: Placebo
Duration of treatment: 1×12 weeks (84 days)
Diagnosis and main criteria for inclusion of Subjects:
Women, 18 to 50 years old, with uterine fibroids documented by transvaginal or abdominal ultrasound at screening with at least 1 uterine fibroid with largest diameter 3 cm and Heavy Menstrual Bleeding (HMB) 80 ml were eligible for enrolment in the study.
Number of Women: 279 subjects
Screening Period:
Following screening visit 1 (Visit 1), there was a screening period of up to 90 days to arrange for complete results of all baseline assessments. During the screening period, subjects were to demonstrate eligibility including presence of at least 1 uterine fibroid of maximum 3 cm diameter and a diagnosis of HMB, defined as menstrual blood loss 80 ml assessed by menstrual pictogram (MP) during the bleeding episode following the screening visit 1 (Visit 1). Every effort should be made to keep the duration of the screening period to a minimum.
Treatment Period:
Eligible subjects were equally randomized to one of the treatment groups (Placebo, 0.5 mg, 1 mg, 2 mg, or 4 mg Compound 1). Treatment was started during the first week of the menstrual cycle following randomization. The treatment period consisted of 12 weeks (84 days) of daily tablet intake.
Efficacy Measurement:
 daily documentation of bleeding intensity (electronic diary or eDiary)
 Menstrual Pictogram MP (electronic diary or eDiary)
 collection of sanitary products for analysis of menstrual blood loss with alkaline hematin (AH) method Time to onset of amenorrhea:
Onset of amenorrhea is defined by the first day for which the menstrual blood loss (assessed by MP) for all subsequent 28-day periods up to the end of the treatment period is less than 2 ml.
The primary objective estimates the dose-response curve based on the primary endpoint women with amenorrhea by dose.
Results:
Compound 1 has demonstrated dose-dependent induction of amenorrhea in subjects. Heavy menstrual bleeding is reduced quickly and sustainably. Most subjects even achieved amenorrhea already during treatment, see FIG. 3.
At the End of Treatment (EoT=3 months), 91.65% of the subjects treated with 2 mg of Compound 1 show an amenorrhea (<2 ml bleeding), see table 2.

TABLE 2

Compound 1 induced Amenorrhea (<2 ml) at EoT vs Ulipristal Acetate (UPA)

| Parameter | Placebo | 0.5 mg Cp01 | 1 mg Cp01 | 2 mg Cp01 | 4 mg Cp01 | 5 mg Ulipristal Acetate* |
|---|---|---|---|---|---|---|
| Amenorrhea (<2 ml) at EoT (%) 12 Weeks | 7.63 | 66.63 | 87.09 | 91.65 | 89.81 | ~75 |

Cp01: Compound 01
EoT: End of Treatment
*Data from Jacques Donnez et al

Comparable study and results thereof were reported by Jacques Donnez et al. in "The new England journal of medicine". (Donnez, Jacques et al*. "Ulipristal Acetate versus Leuprolide Acetate for Uterine Fibroids". *N. Engl. J. Med.* (2012): 366; 5.)

TABLE 3

Ulipristal Acetate (UPA) induced Amenorrhea (<2 ml) at EoT

| Parameter | Ulipristal Acetate 5 mg |
|---|---|
| ≤2 ml, indicating Amenorrhea - no./total no. (%) EoT 13 Weeks | 70/93 (75) |

EoT: End of Treatment

Figure 3:
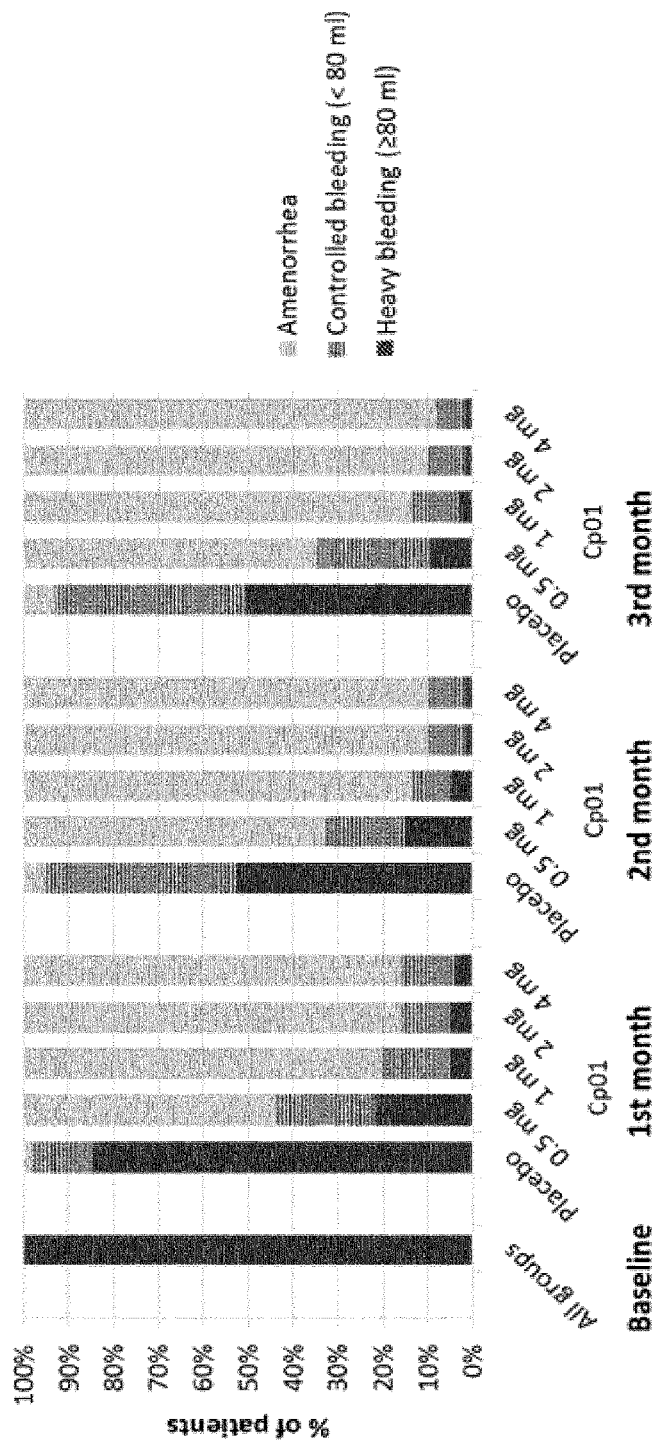

FIG. 3: Compound 1 Efficacy on Heavy menstrual bleeding (HMB)
Cp01: Compound 01

Example 5 Amenorrhea 3-Month Vs 6-Month Treatment with Compound 1

A randomized, parallel-group, double-blind, placebo-controlled, multi-center study to assess efficacy of a dose of 2 mg of Compound 1 where primary efficacy variable is Amenorrhea, in subjects with uterine fibroids over 3 months [1×12 weeks] and 6 months [2×12 weeks without treatment break].

Study protocol (No 17541):
Test drug: Compound 1 Doses: 2 mg, once daily
Route of administration: Oral
Duration of treatment: 2×12 weeks without treatment break
Reference drug: Placebo
Duration of treatment: 1×12 weeks (84 days)
Diagnosis and main criteria for inclusion:
Women, 18 to 50 years old, with uterine fibroids documented by transvaginal or abdominal ultrasound at screening with at least 1 uterine fibroid with largest diameter 3 cm and Heavy Menstrual Bleeding (HMB) 80≥ ml were eligible for enrolment in the study.
Number of Women: 174 subjects
Screening Period:
Following screening visit 1 (Visit 1), there was a screening period of up to 60 days to arrange for complete results of all baseline assessments. During the screening period, subjects were to demonstrate eligibility including presence of at least 1 uterine fibroid of maximum 3 cm diameter and a diagnosis of HMB, defined as menstrual blood loss 80 ml assessed by menstrual pictogram (MP) during the bleeding episode following the screening visit 1 (Visit 1). Every effort should be made to keep the duration of the screening period to a minimum. Screening period was up to 60 days. Eligible subjects were randomized.
Treatment Period:
Eligible subjects will be equally randomized to one of the treatment groups (Placebo, 2 mg of Compound 1). Treatment will start during the first week of the menstrual cycle following randomization. The treatment period will consist of 1×12 and 2×12 weeks (84 days) of daily tablet intake.
Treatment A1: 2 mg of Compound 1 (12 weeks), 2 mg of Compound 1 (12 weeks) without treatment break
Treatment A2: Placebo (12 weeks), 2 mg of Compound 1 (12 weeks).
Efficacy Measurement:
daily documentation of bleeding intensity (electronic diary or eDiary)
Menstrual Pictogram MP (electronic diary or eDiary).
Time to onset of amenorrhea:
Onset of amenorrhea is defined by the first day for which the menstrual blood loss (assessed by MP) for all subsequent 28-day periods up to the end of the treatment period is less than 2 ml.

The primary objective is to estimate the dose-response curve based on the primary endpoint women with amenorrhea by dose and the presence of amenorrhea after 1×12 weeks and after 2×12 weeks of treatment.

Results:
The primary endpoint amenorrhea (no/yes) was based on the bleeding intensity recorded in the eDiary/Daily bleeding diary.
Based on preliminary data in a subjects, it was found that Compound 1 continued to demonstrate a dose-dependent induction of amenorrhea in subject until 6 months of treatment wherein amenorrhea observed after 1×12 weeks is maintained.

Patients treated with Compound 1 for a period of 6 months (2×12 weeks without treatment break) do not show increased rates of adverse events with regard to ovarian cysts or bleeding. As well, the rate of subjects with endometrial thickness above 18 mm was not found to be increased.

Example 6: Endometrium Thickness 3-Month Vs 6-Month Treatment with Compound 1

A randomized, parallel-group, double-blind, placebo-controlled, multi-center study to assess efficacy of a dose of 2 mg of Compound 1 where primary efficacy variable is Endometrium thickness, in subjects with uterine fibroids over 3-month vs 6-month with or without treatment break.

Study Protocol (No 17541):
Test drug: Compound 1
Doses: 2 mg, once daily
Route of administration: Oral
Duration of treatment: 2×12 weeks (A1) or 1×12 weeks (A2) without treatment break
Placebo: no treatment
Diagnosis and main criteria for inclusion:
Women, 18 to 50 years old, with uterine fibroids documented by transvaginal or abdominal ultrasound at screening with at least 1 uterine fibroid with largest diameter 3 cm and Heavy Menstrual Bleeding (HMB) 80≥ ml were eligible for enrolment in the study.
Number of Women: 13 subjects having finished the treatment so far.
Screening Period:
Following screening visit 1 (Visit 1), there was a screening period of up to 60 days to arrange for complete results of all baseline assessments. During the screening period, subjects were to demonstrate eligibility including presence of at least 1 uterine fibroid 3 cm in maximum diameter and a diagnosis of HMB, defined as menstrual blood loss 80 ml assessed by menstrual pictogram (MP) during the bleeding episode following the screening visit 1 (Visit 1). Every effort should be made to keep the duration of the screening period to a minimum. Screening period was up to 60 days. Eligible subjects were randomized.
Treatment Period:
Eligible subjects were equally randomized to one of the treatment groups (Placebo, 2 mg of Compound 1). Treatment period was started during the first three days of the bleeding episode following randomization or ongoing at randomization. The treatment period will consist of 3 months (12 weeks) or 6 months [2×12 weeks (84 days)] of daily tablet intake without treatment break.
Treatment A1: 2 mg of Compound 1 (12 weeks), 2 mg of Compound 1 (12 weeks).
Treatment A2: Placebo (12 weeks), 2 mg of Compound 1 (12 weeks).
Follow-Up Period:
After the end of treatment period, subjects were followed up for 12 weeks. At the end of follow-up, an endometrial biopsy was performed (unless a hysterectomy had been performed). If spontaneous menstrual bleeding did not occur until 10 weeks after the end of treatment, an additional transvaginal ultrasound (TVU) and endometrial biopsy was performed followed by induction of bleeding, if indicated. In case of findings that require further follow-up, additional visits was scheduled according to normal standard practice. Any decisions about surgical treatment were made by the patient/subject and the investigator. Surgery was not considered as part of the study procedure, and was not considered an adverse event (AE).

Figure 4:
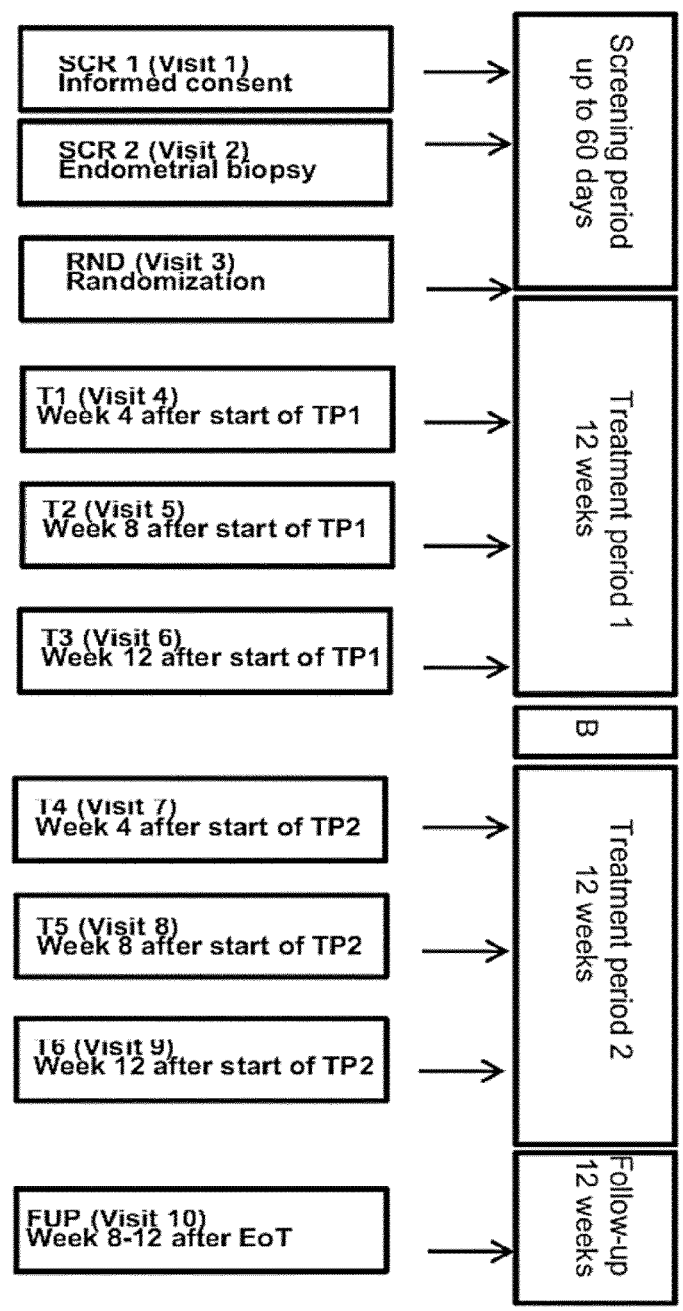

Efficacy Measurement:
endometrial biopsies,
cervical smear,
transvaginal ultrasound (TUV) (endometrial thickness, ovaries).
FIG. 4: Study Design Overview
EoT: End of Treatment
FUP: Follow-up visit 1
RND: Randomization visit
SCR1, 2: Screening visits 1, 2
T1, 2, 3, 4, 5 and 6: Treatment visits 1, 2, 3, 4, 5, 6
B: Break, duration depending on group allocation (no break for groups A)
TP1, 2: Treatment period 1, 2
Results:

The study results disclosed above are still blinded. Thus, considering the results, subjects treated 6 months with Compound 1 cannot be differentiated from Subjects treated 3 months with Compound 1 followed by treatment with placebo.

Based on preliminary data, it was found that in the 13 subjects no treatment-emergent critical endometrial findings occurred wherein endometrial size was not increased above 18 mm. Indeed, endometrial size above 18 mm is seen by the Food and Drug Administration (FDA) as the threshold for a risk of endometrial hyperplasia and trigger additional diagnostic procedures.

Example 7: Endometrium Thickness 2×3-Month Treatment with Compound 1 and Break Period A randomized, parallel-group, double-blind, placebo-controlled, multi-center study to assess efficacy of a dose of 2 mg of Compound 1 where primary efficacy variable is Endometrial thickness, in subjects with uterine fibroids over 2×3-month with break period allowing bleeding episode.

Study Protocol (No 17541):
Test drug: Compound 1
Doses: 2 mg, once daily
Route of administration: Oral
Duration of treatment: 2×3-month [2×12 weeks]+one bleeding episode (B1) and 1×3-month [1×12 weeks] (B2) without treatment break
Placebo: none
Diagnosis and main criteria for inclusion:

Women, 18 to 50 years old, with uterine fibroids documented by transvaginal or abdominal ultrasound at screening with at least 1 uterine fibroid with largest diameter 3.0 cm and heavy menstrual bleeding (HMB) 80☐ mL were eligible for enrolment in the study.

Number of Women: 6 subjects that have finalized the treatment
Screening period: as described in example 6
Treatment Period:

Eligible subjects were equally randomized to one of the treatment groups (Placebo, 2 mg of Compound 1). Treatment period was started during the first three days of the bleeding episode following randomization or ongoing at randomization. The treatment period was consisting of daily tablet intake without treatment break.

Treatment B1: 2 mg of Compound 1 (12 weeks), 1 bleeding episode, 2 mg of Compound 1 (12 weeks).

Figure 5:
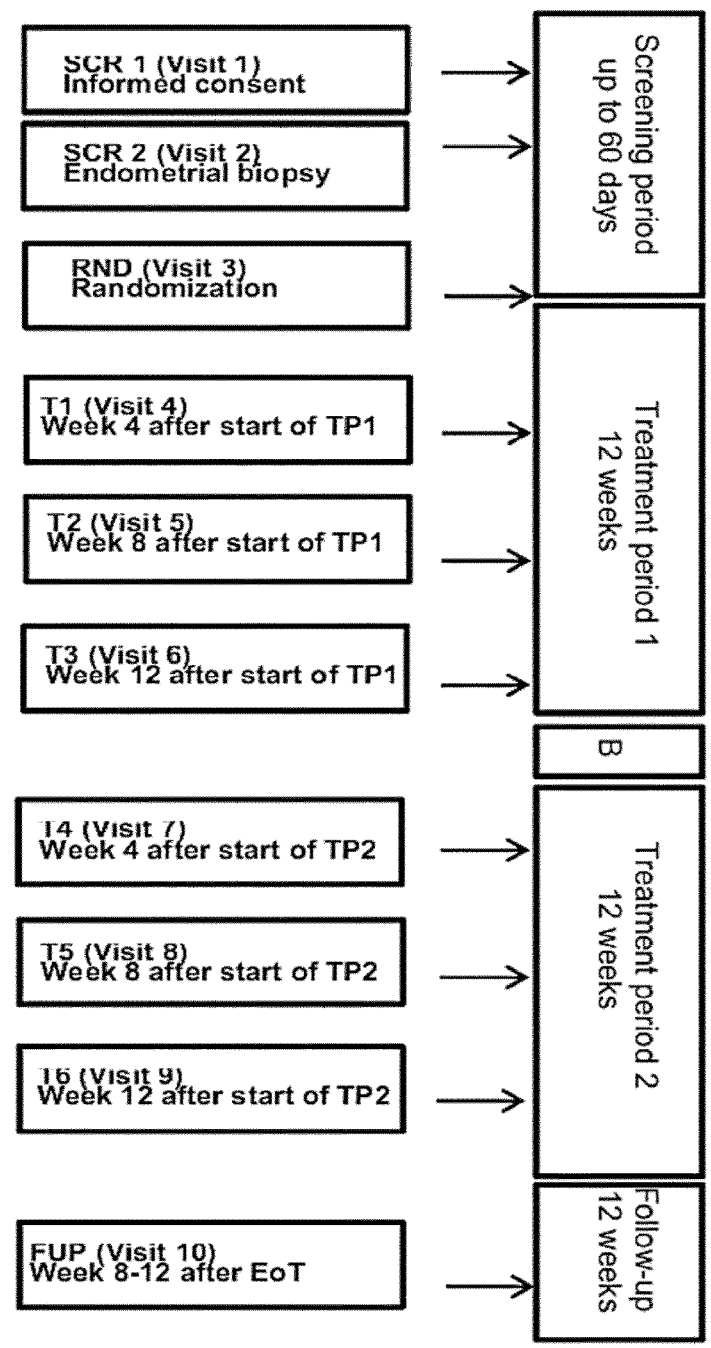

Treatment B2: Placebo (12 weeks), 1 bleeding episode, 2 mg of Compound 1 (12 weeks).
Follow-Up Period:
as described in example 6
Efficacy Measurement:
endometrial biopsies,
cervical smear,
transvaginal ultrasound (TUV) (endometrial thickness, ovaries).
FIG. 5: Study Design Overview
EoT: End of Treatment visit
FUP: Follow-up visit 1
RND: Randomization visit
SCR1, 2: Screening visit 1, 2
T1, 2, 3, 4, 5, 6: Treatment visit 1, 2, 3, 4, 5, 6
B: Break period, duration depending on group allocation
TP1, 2: Treatment period 1, 2
Results:

The study results disclosed above are still blinded. Thus, subjects treated 2×3 months with Compound 1 followed with treatment break cannot be differentiated from subjects treated during a single period of 3 months with Compound 1 followed by placebo.

It was found that in the 6 subjects no treatment-emergent critical endometrial findings occurred wherein endometrial size was not increased above 18 mm. Indeed, endometrial size above 18 mm is seen by the Food and Drug Administration (FDA) as the threshold for a risk of endometrial hyperplasia and trigger additional diagnostic procedures.

Example 8 Change in Volume of Largest Fibroid 3-Month Treatment with Compound 1

A randomized, parallel-group, double-blind, placebo-controlled, multi-center study to assess efficacy of different doses of Compound 1 where secondary efficacy variable is the change in volume of the largest fibroid in subjects wherein treatment is of 3 months [1×12 weeks (84 days)].

Study Protocol (No 15788):
Test drug: Compound 1
Doses: 0.5 mg, 1 mg, 2 mg, or 4 mg once daily
Route of administration: Oral
Duration of treatment: 1×12 weeks (84 days)
Reference drug: Placebo
Duration of treatment: 1×12 weeks (84 days)
Diagnosis and main criteria for inclusion:

Women, 18 to 50 years old, with uterine fibroids documented by transvaginal or abdominal ultrasound at screening with at least 1 uterine fibroid with largest diameter 3 cm and heavy menstrual bleeding (HMB) 80 ml were be eligible for enrolment in the study.

Number of Women: 279 subjects
Screening period: as described in example 4
Treatment period: as described in example 4
Efficacy Measurement:

The secondary efficacy variable is the percent change in volume of the largest fibroid compared to baseline (measured by MRI and TVU)
MRI: Magnetic Resonance Imaging
TVU: Transvaginal/abdominal ultrasound
Transvaginal/Abdominal Ultrasound:

Ultrasound examination was performed consistent with the schedule of procedures (Table 1). For each subject, the most appropriate ultrasound method (transvaginal or abdominal) was used depending on fibroid location and this method was consistently used throughout the study. The same ultrasound machine (per site) should be used throughout the study.

The 3 largest fibroids were identified during the screening period. The largest transverse, longitudinal, and antero-posterior diameters of these 3 fibroids were documented at each ultrasound examination for volume calculation.

The dimensions of the uterus were also documented at the same time points. This is of particular importance in subjects with multiple small fibroids.

Magnetic Resonance Imaging:

Pelvic MRI was performed for volume measurements of the uterus and fibroids at the specified time points in all subjects (see table 1). A pelvic MRI without contrast agent administration was performed with a good diagnostic quality preferably on Tesla scanners. Images were sent to the dedicated Imaging Core Laboratory for further evaluation. Volume measurements of the uterus and fibroids were performed centrally by independent radiologist(s).

TABLE 3

MRI and Utrasound Study design overview:

| | Screening period | | | Treatment period | | | | Follow-up period | |
|---|---|---|---|---|---|---|---|---|---|
| | | | | | | Visit | | | |
| | SCR1 | SCR2 | RND | T1 | T2 | EoT | FUP1 | FUP2 | FUP3[h] |
| | | | | | | Visit number | | | |
| | 1 | 2 | 3 | 4 | 5 | 6 | 7 | 8 | Phone contact | 9 |
| Timing | | | | Week 4 | Week 8 | Week 12 | Timing depends on randomization of biopsy sample[e] | 12 weeks after last study drug intake | To agree on the timing of Visit 9 | 21-24 weeks after last study drug intake |
| Ultrasound examination | X | X | X | X | X | X | X | X | | X |
| MRI[f] | | | | X | | X[f] | | | | X[f] |

EoT: End of Treatment visit
FUP1, 2, 3: Follow-up visit 1, 2, 3
RND: Randomization visit
SCR1, 2: Screening visit 1, 2
T1, 2: Treatment visit 1, 2

Results:

Compound 1 has demonstrated dose-dependent reduction in fibroid size during treatment. The effect is confirmed by both methods i.e. MRI and TVU. Effect is partially sustained during follow-up, see FIGS. 8 and 7.

Figure 6:
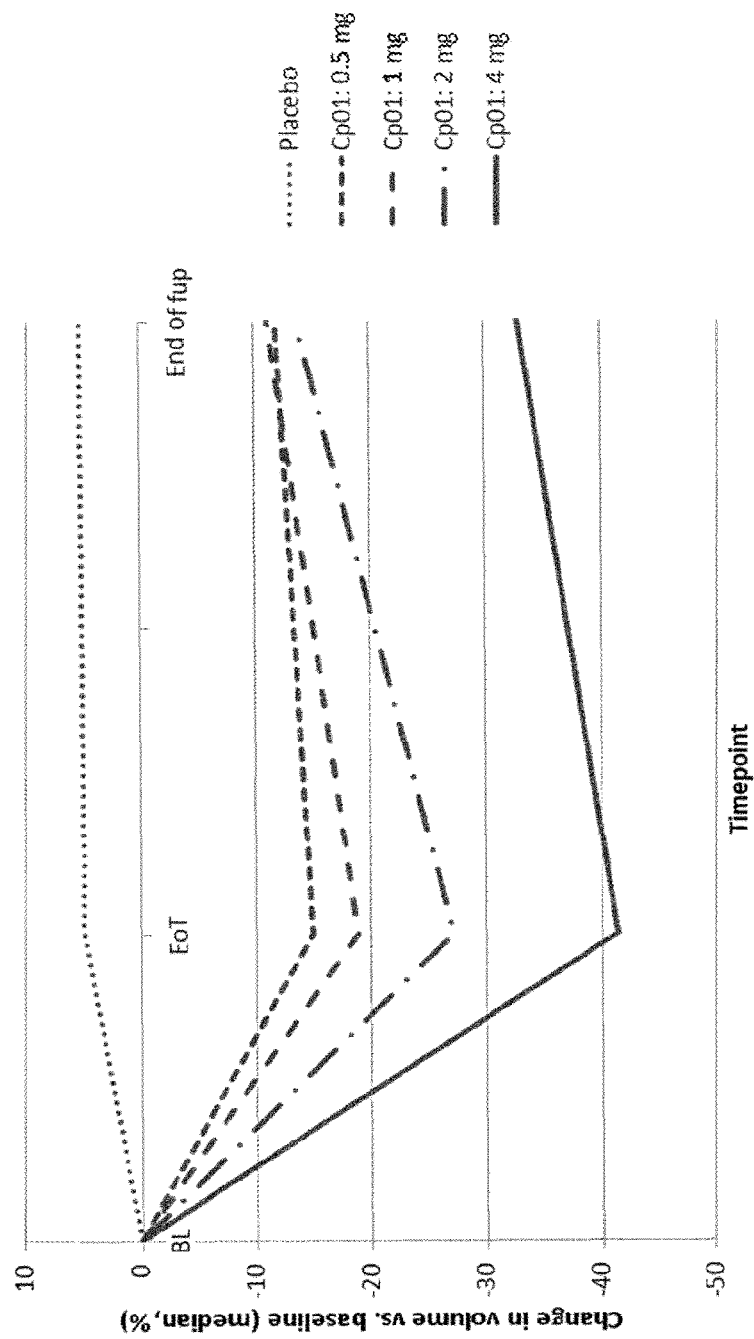

FIG. 6: Percent Change in Volume of Largest Fibroid (MRI)
BL: Baseline
EoT: End of Treatment
End of fup: End of follow up
Cp01: Compound 1

Figure 7:
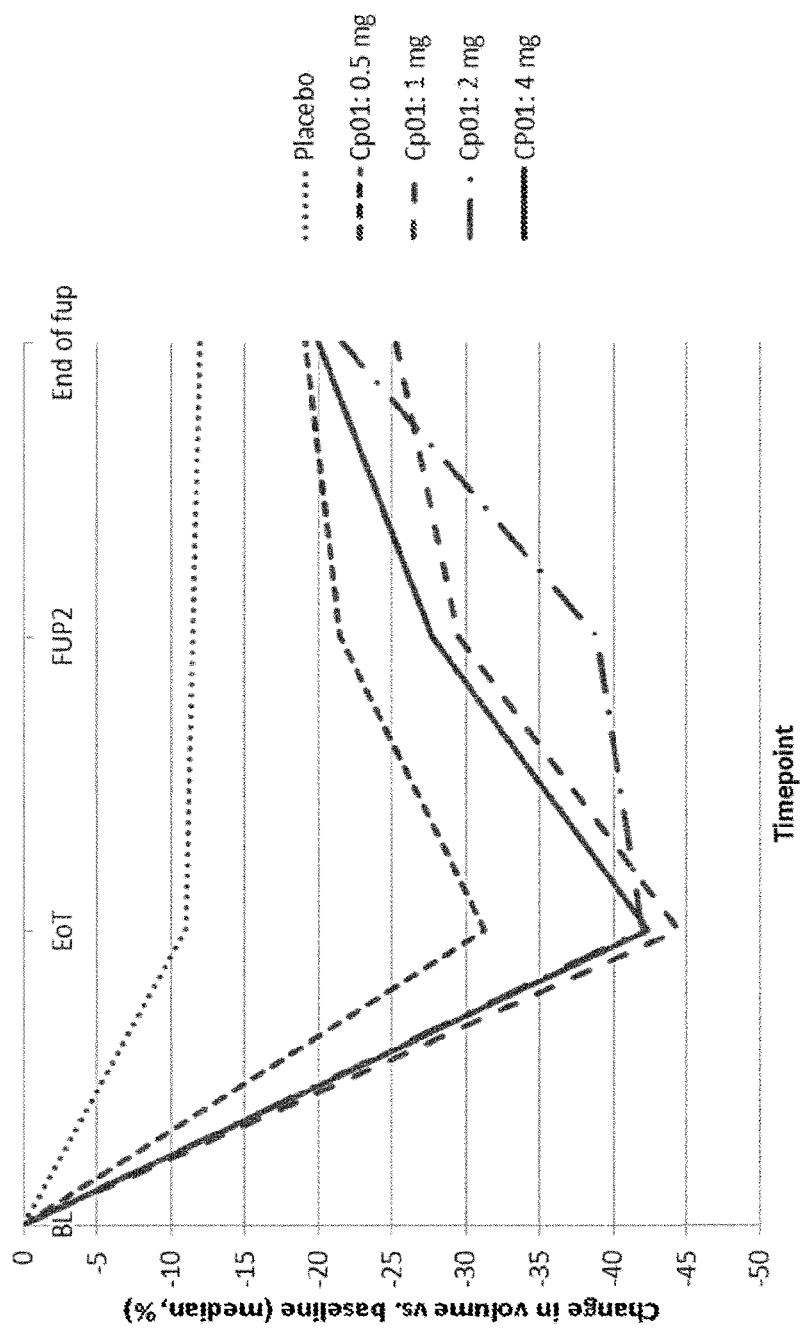

FIG. 7: Percent Change in Volume of Largest Fibroid (TVU)
BL: Baseline
EoT: End of Treatment
FUP2: Follow-up visit
End of fup: End of follow up
Cp01: Compound 1

The invention claimed is:

1. A method for treating uterine fibroids comprising administering to a patient in need thereof a pharmaceutical composition comprising (11β,17β)-17-Hydroxy-11-[4-(methylsulphonyl)phenyl]-17-(pentafluoroethyl)estra-4,9-dien-3-one (Compound 1) of formula

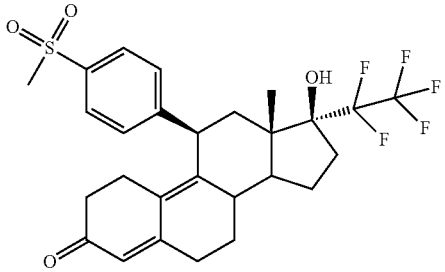 [SMILES: C[C@]12C[C@H](c3ccc(S(C)(=O)=O)cc3)C3=C4CCC(=O)C=C4CCC3C1CC[C@@]2(O)C(F)(F)C(F)(F)F]

or salts, solvates or solvates of the salts, or all crystal modifications thereof, comprising the steps of:

administering the pharmaceutical composition daily during a period of twelve (12) weeks and
discontinuing the administration until one (1) bleeding episode occurs.

2. The method of claim 1 wherein the administering step and the discontinuing step are repeated at least one (1) time following the bleeding episode.

3. The method of claim 1, wherein Compound 1 is administered at a daily dose of 1 mg to 5 mg.

4. The method of claim 3, wherein Compound 1 is administered at a daily dose of about 2 mg.

5. The method of claim 1, wherein the size of the uterine fibroids is reduced following treatment.

6. The method of claim 1, wherein symptoms of uterine fibroids are reduced during treatment.

7. The method of claim 6, wherein the symptoms are selected from the group consisting of heavy menstrual bleeding, pelvic pain or pressure, backache or leg pains or pressures, prolonged menstrual periods, frequent urination or constipation.

8. The method of claim 7, wherein the symptom is heavy menstrual bleeding.

9. The method of claim 8, wherein amenorrhea occurs after about three (3) weeks.

10. A method for treating uterine fibroids comprising administering to a patient in need thereof a pharmaceutical composition comprising (11β,17β)-17-Hydroxy-11-[4-(methylsulphonyl)phenyl]-17-(pentafluoroethyl)estra-4,9-dien-3-one (Compound 1) of formula

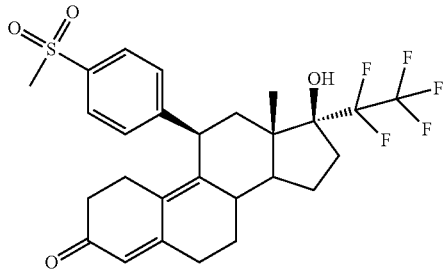 [SMILES: C[C@]12C[C@H](c3ccc(S(C)(=O)=O)cc3)C3=C4CCC(=O)C=C4CCC3C1CC[C@@]2(O)C(F)(F)C(F)(F)F]

or salts, solvates or solvates of the salts, or all crystal modifications thereof, comprising the steps of:
administering the pharmaceutical composition daily during a period of twenty-four (24) weeks and discontinuing the administration until (2) bleeding episode occur.

11. The method of claim 10 wherein the administering step and the discontinuing step are repeated at least one (1) time following the bleeding episode.

12. The method of claim 10, wherein Compound 1 is administered at a daily dose of 1 mg to 5 mg.

13. The method of claim 12, wherein Compound 1 is administered at a daily dose of about 2 mg.

14. The method of claim 10, wherein the size of the uterine fibroids is reduced following treatment.

15. The method of claim 10, wherein symptoms of uterine fibroids are reduced during treatment.

16. The method of claim 15, wherein the symptoms are selected from the group consisting of heavy menstrual bleeding, pelvic pain or pressure, backache or leg pains or pressures, prolonged menstrual periods, frequent urination or constipation.

17. The method of claim 16, wherein the symptom is heavy menstrual bleeding.

18. The method of claim 17, wherein amenorrhea occurs after about three (3) weeks.

\* \* \* \* \*